(12) United States Patent  (10) Patent No.: US 8,538,107 B2
Röttger  (45) Date of Patent: Sep. 17, 2013

(54) METHOD FOR VISUALIZING A SEQUENCE OF TOMOGRAPHIC VOLUME DATA RECORDS FOR MEDICAL IMAGING

(75) Inventor: Stefan Röttger, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 1296 days.

(21) Appl. No.: 12/076,707

(22) Filed: Mar. 21, 2008

(65) Prior Publication Data

US 2008/0232666 A1    Sep. 25, 2008

(30) Foreign Application Priority Data

Mar. 23, 2007  (DE) .......................... 10 2007 014 133

(51) Int. Cl.
    *G06K 9/00*    (2006.01)
(52) U.S. Cl.
    USPC .......................................... 382/131; 382/128
(58) Field of Classification Search
    USPC ......... 382/128, 131, 132, 130, 133; 600/420, 600/425
    See application file for complete search history.

(56) References Cited

U.S. PATENT DOCUMENTS

| | | | | |
|---|---|---|---|---|
| 5,509,412 | A * | 4/1996 | Bahn .............................. | 600/419 |
| 6,073,042 | A * | 6/2000 | Simonetti ...................... | 600/420 |
| 2004/0126007 | A1 * | 7/2004 | Ziel et al. ...................... | 382/154 |
| 2005/0024724 | A1 * | 2/2005 | Kim et al. ...................... | 359/462 |
| 2005/0075846 | A1 * | 4/2005 | Kim ................................ | 703/1 |
| 2005/0249393 | A1 | 11/2005 | Kropfeld | |
| 2007/0012101 | A1 * | 1/2007 | Rottger et al. .............. | 73/170.24 |
| 2007/0154075 | A1 * | 7/2007 | Matsumoto ................... | 382/128 |
| 2007/0165920 | A1 * | 7/2007 | Gering et al. ................. | 382/128 |
| 2009/0103793 | A1 * | 4/2009 | Borland et al. ............... | 382/131 |

FOREIGN PATENT DOCUMENTS

| | | |
|---|---|---|
| DE | 102004022902 | 12/2005 |
| DE | 102005024949 | 12/2006 |
| WO | WO 2006099490 A1 * | 9/2006 |

OTHER PUBLICATIONS

German Office Action issued Jan. 15, 2008.

* cited by examiner

*Primary Examiner* — Jason McCormack
(74) *Attorney, Agent, or Firm* — Harness, Dickey & Pierce, PLC

(57) ABSTRACT

A method for visualizing a sequence of tomographic volume data records for medical imaging, which were recorded in temporal sequence with administration of contrast agents in vessels in an object volume, is provided. At least one extremal value and one time value are determined from the temporal sequence of the measured signal values for each voxel of the object volume, the time value describing a time lag of the extremal value compared to a fixed time during the recording of the volume data records. Each combination of time value and extremal value is assigned a color value and opacity value by a multi-dimensional transfer function. The transfer function is applied to the previously determined time and extremal values so that each voxel of the object volume is assigned a color value and opacity value. The voxel with the respective opacity and color values are displayed using volume rendering.

26 Claims, 5 Drawing Sheets

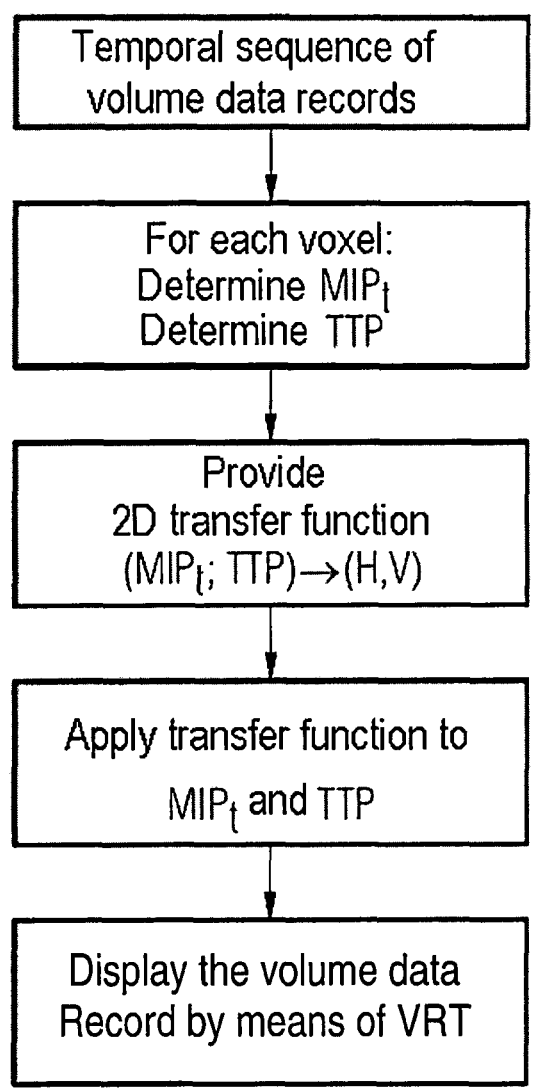

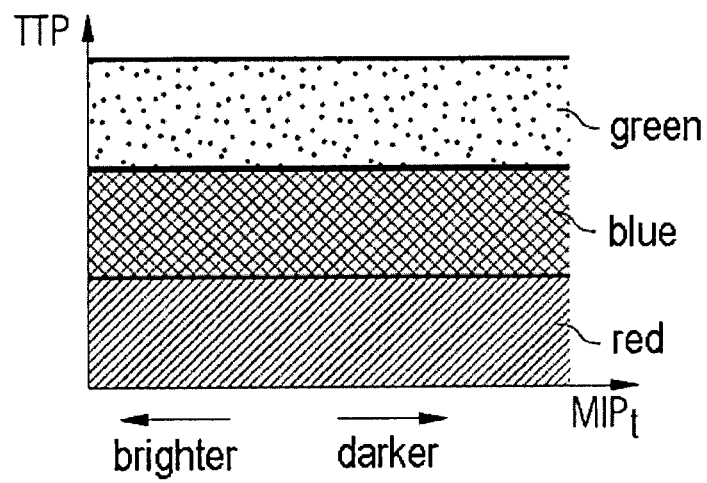
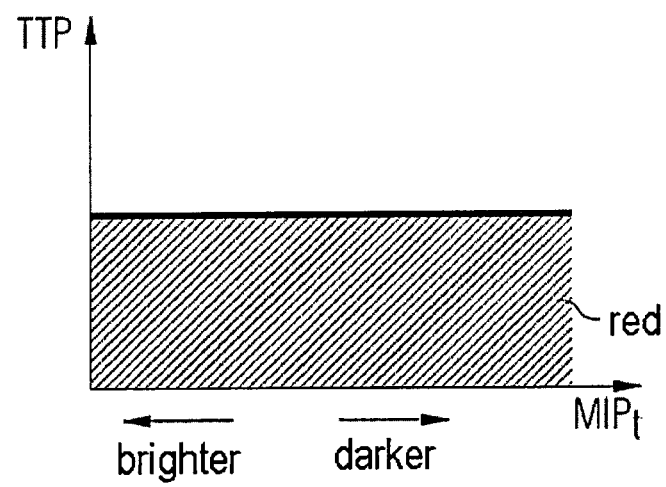

METHOD FOR VISUALIZING A SEQUENCE OF TOMOGRAPHIC VOLUME DATA RECORDS FOR MEDICAL IMAGING

PRIORITY STATEMENT

The present application hereby claims priority under 35 U.S.C. §119 on German patent application number DE 10 2007 014 133.7 filed Mar. 23, 2007, the entire contents of which is hereby incorporated herein by reference.

BACKGROUND

1. Field

Embodiments of the present invention relate to methods for visualizing a sequence of tomographic volume data records for medical imaging so that at least one temporal sequence of measured signal values is present for each voxel of the object volume. The tomographic volume data records are recorded in temporal sequence with administration of contrast agents in vessels in an object volume.

2. Description of the Conventional Art

Conventionally, tomographic imaging techniques, such as computed tomography (CT) or magnetic resonance imaging (MR), are used to visualize vessels such as arteries and/or veins. By recording a plurality of tomographic volume data records after the injection of a contrast agent into the vascular system, the dispersion of the contrast agent can be traced and possible narrowings in the vascular system can be recognized. In a typical cardiac examination, 20 to 30 tomographic MR volume data records (3D image data records) are recorded. These data records are saved, loaded for later visualization and processed for imaging. Visualization of the temporal development of the dispersion of the contrast agent has very high memory and computing time requirements. Accordingly, visualization of the temporal development of the dispersion of the contrast agent has been possible only to a limited extent in real time without data compression.

SUMMARY

At least one embodiment of the present invention specifies a method for visualizing a sequence of tomographic volume data records for medical imaging, which were recorded in temporal sequence with administration of contrast agents in vessels in an object volume. Embodiments of the present invention allow visualization of the temporal progression of the dispersion of the contrast agent and/or improved differentiation between veins and arteries in real time, with less demand on memory and computing requirements.

At least one embodiment of the proposed method assumes a sequence of tomographic volume data records for medical imaging—recorded in temporal sequence with administration of contrast agents in vessels in an object volume—such that at least one temporal sequence of measured signal values is present for each voxel or volume element of the examination volume. According to this embodiment, these signal values correspond to the recorded measured values of the respective imaging system. Hence these signal values correspond to x-ray attenuation levels (=Hounsfield units) in the case of CT volume data records and they correspond to nuclear spin signals in the case of MR volume data records. In the proposed method, at least one extremal value and one time value are determined for each voxel from the temporal sequence of the measured signal values for this voxel. The time value describes a time lag of the extremal value or a value derived therefrom compared to a fixed time during the recording of the volume data records. By way of example, the fixed time can be the start time of the recording of the first volume data record or the start time of the injection of the contrast agent. The time lag between the time of injection of the contrast agent and the maximum value (as extremal value) is also known as the time-to-peak (TTP). However, a different time value, such as the time lag between the time of injection and the time of the signal value of the voxel reaching a predetermined or given fraction of the extremal value, can be defined as well. In one embodiment, the maximum value of the signal (=MIPt: maximum intensity projection over time) is defined as the extremal value. The maximum value corresponds to the maximum value of the attenuation in CT volume data records, and the maximum value of the magnetic resonance signal in the case of MR volume data records, in each case in the correspondingly considered volume element.

Furthermore, embodiments of the present invention provide an at least two dimensional transfer function. Each combination of time value and extremal value are assigned a color value and opacity value. By way of example, this transfer function can be an LUT (look-up table). The transfer function is applied to the previously determined time and extremal values so that each voxel of the examination volume is assigned a color value and opacity value. The voxels are then displayed on a monitor with these color and opacity values, using a volume rendering technique.

At least one embodiment of the present invention thus generates at least two parameter volumes from the initial data, for example, the sequence of the tomographic volume data records. One of the at least two parameter volumes comprises the extremal value determined for each voxel. Another of the at least two parameter volumes comprises the time value determined for each voxel. The initial data are no longer required after this step. In this case, voxels that are determined not to have a significant change of the signal value over time are either displayed with their original value—converted to grayscale—or masked out, since they do not represent a vessel. This can also be carried out by the transfer function (opacity value=0). The individual tomographic volume data records, which the method assumes may, in this case, already have had the background removed from them by subtracting a mask image (a tomographic volume data record of the same object volume without administration of contrast agent) from these angiographic images. This technique is known as digital subtraction angiography.

By the subsequent application of the two-dimensional transfer function to these at least two parameter volumes, each voxel is assigned an opacity value and a color value. Established volume rendering techniques, which are known to a person skilled in the art in this particular field of medical imaging, can be used for the subsequent imaging. The color value for the respective voxel is a measure of the time value determined for this voxel, and the opacity value is a measure of the extremal value determined for this voxel. In this case, a linear or nonlinear relationship can be used for the opacity values in a known manner. The time values can also be mapped onto the color values in a linear or nonlinear fashion.

In the illustrated rendered image, the temporal progression of the contrast agent diffusion, and thus the perfusion, hence become apparent, provided that the color value(s) have been appropriately assigned. The temporal sequence is apparent from the color, and the anatomy is apparent from the opacity. By way of example, a small time value corresponding to an early time can, in this case, be displayed in a red color and a large time value corresponding to a later time can be displayed in a blue color. Time values between these two extremes can then be represented by the corresponding intermediate colors. Of course, different color distributions are also possible for visualizing the temporal progression of the perfusion. On the other hand, the determined extremal values are preferably displayed using an opacity scheme, in which the opacity—in the case of a maximum value as an extremal value—increases with increasing magnitude of the maximum value. Hence, larger maximum values are preferably displayed more opaquely, while smaller maximum values are displayed more transparently.

Embodiments of the present invention also makes it possible to mask out specific time intervals from the display. This can be implemented by a corresponding step in the transfer function. By way of example, all time values which lie above the step (that is to say later times) can be masked out by the corresponding entries in transfer function being set to zero, for example. This allows visualizing the contrast agent dispersion until a specific time, or conversely, from a specific time. In one alternative embodiment of the proposed method, such a step in the transfer function can be shifted interactively or automatically. In this way the actual temporal progression of the perfusion can be simulated continuously. It is, of course, also possible in this case to display only one time interval or time window, and optionally also to move this, by using two steps.

Arteries-vein separation can also be carried out using such a step in the transfer function. The fact that arteries are highlighted with the contrast agent at earlier times and veins are highlighted with the contrast agent at later times is utilized in this case. By suitable arrangement of the step in the transfer function, it is, for example, possible to display only the arteries, by masking out the venous part of the vascular system via the time value. The precise definition of the threshold is carried out interactively by the medical practitioner. A suitable color coding of the time values using the transfer function can also be used to separate arteries and veins in which, for example, all times below a given threshold are colored red and all times above the given threshold are colored blue. By use of this color coding, the arteries then appear red and the veins appear blue in the displayed rendered image.

The temporal progressions recorded by the sequence of tomographic volume data can thus be displayed with small memory and shorter computing time requirements by use of the embodiments of the present invention. The shift of a step in the multidimensional transfer function additionally allows visualization of a film-like display on the basis of only one volume data record. Hence, the entire method can be carried out in real time so that possible interactive rotations of the rendered display can also be carried out in real time by the user. The same applies to a change of the step or windowing in the transfer function. Furthermore, the method allows an improved display of the vascular system, for example by masking out the veins or by visualizing them in a different color to the arteries. The different components of the vascular system or else the heart are thus more easily recognizable.

By way of example embodiments of the method can be implemented in an image computer, by providing corresponding modules for the determination of the extremal value and the time value, the multidimensional transfer function and a module for application of the transfer function to the determined extremal and time values in the image computer. A suitable rendering module generally already exists in such an image computer for the tomographic imaging of 3D image data records. Furthermore, an interactive user interface—via which the user can change the transfer function—should be provided. Via the interactive user interface, the user can insert steps into the transfer function and/or shift them there interactively or automatically, using a suitable manipulation module. In this case, the image computer is connected via a graphics card to an image display unit in a suitable manner, in particular a color monitor, for the visualization of the rendered volume data record.

BRIEF DESCRIPTION OF THE DRAWINGS

The present invention will be explained again briefly in the following text on the basis of one exemplary embodiment and in conjunction with the drawings, in which FIG. 1 schematically shows an exemplary procedure for carrying out a method according to an embodiment of the present invention;

FIG. 2 shows a schematic illustration of an example of the two-dimensional transfer function;

FIG. 5 shows a schematic illustration of a further example of a two-dimensional transfer function.

DETAILED DESCRIPTION OF THE EXAMPLE EMBODIMENTS

Figure 3:
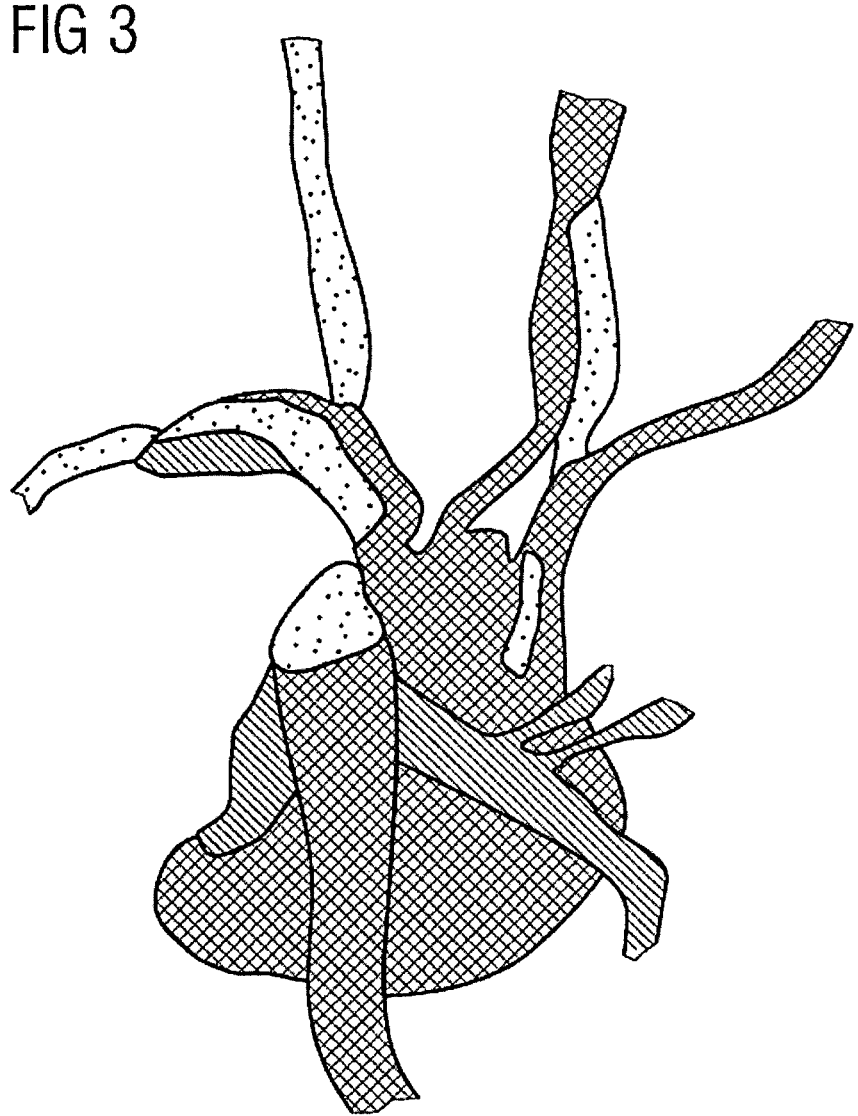
FIG. 3 shows an example of an image generated by the method according to an embodiment of the present invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Embodiments of the present invention will be explained again briefly in the following text on the basis of the exemplary procedure illustrated in FIG. 1. The method will be described assuming a sequence of 3D volume data records, which can, for instance, be generated by a computed tomography scanner or MR scanner. Each volume data record in this sequence comprises a three-dimensional matrix of attenuation values, wherein each attenuation value corresponds to a specific volume element or voxel of the examined volume of the patient's body from which the volume data record was recorded. Using the injection of a contrast agent into the patient's vascular system as a starting point, the sequence may comprise, for example, approximately 30 volume data records recorded at constant and known intervals after the injection of the contrast agent. Hence, each volume data record shows a different time after the injection of the contrast agent, so the temporal dispersion of the contrast agent in the vascular system can be observed from all the volume data records. Due to the administration of contrast agent, much stronger attenuation values are obtained in the vessels compared to the surrounding soft tissue and bones, so that the vessels can be distinguished from this surrounding tissue and bones by the magnitude of these attenuation values.

In the sequence of volume data records, identical matrix positions correspond in a known manner to identical voxels of the examination volume. For each voxel, the maximum achieved attenuation value from the sequence of volume data records is now determined using the embodiments of the present invention. This technique is also known as MIP (maximum intensity projection) over time. At the same time, the time at which this maximum value occurs in the respective voxel is determined. This is carried out on the basis of the known time instant after the starting time at which the associated volume data record containing the maximum value of the corresponding voxel was recorded. This time is also known by the abbreviation TTP (time to peak).

A (new) volume data record is obtained by this determination, in which each voxel of the examination volume has an associated maximum value and time value. Alternatively, this can also be two volume data records, each containing only the time values or only the maximum values. Voxels, whose determined maximum value lies below a given threshold, are set to zero in this case. These are voxels in which the contrast agent highlighting does not occur, for example, voxels which do not represent vessels or represent air and are thus of no interest for later imaging.

Embodiments of the present invention use a two-dimensional transfer function based on scalar and time values. The scalar value in this case corresponds to the determined maximum value. In the transfer function, each combination of maximum value and time value is assigned a color value and an opacity value. The setup of the opacities in this case is linear with respect to the scalar values and constant with respect to the time values. Different TTP times are imaged in different colors so that the temporal progression of the perfusion is apparent from the colors, that is to say the TTP value is mapped onto the hue parameter in the HSV color space. By application of the transfer function to the volume data record or sets containing the time and maximum values, each voxel is assigned a corresponding opacity value and color value. The voxels are subsequently displayed with the respective opacity and color values using a suitable volume rendering technique (VRT). In this example, the temporal progression of the perfusion is then apparent from the colors. The transfer of the voxel values to color and opacity values is carried out on the fly in this case during the imaging, using the appropriate VRT method.

For this purpose, FIG. 2 shows an example of a suitable transfer function in a highly schematic illustration. The colors assigned to the TTP values in this case vary from red at an early time via blue to green at a later time. The opacity values vary from transparent for small maximum values to opaque for large maximum values. FIG. 3 shows an example of such imaging, highly schematically in this case on account of color representation not being possible and the lack of rendering capabilities. In FIG. 3, the vessels highlighted by the contrast agent at an earlier time can be (e.g., clearly) distinguished from the vessels highlighted at a later time on the basis of differently assigned colors. In this example, this is indicated by just three different shadings, due to lack of representation possibilities.

As a result of this, the regions of the heart can be distinguished from one another compared to a standard MIP method. Additional interactive windowing of the TTP values with aid of a variable step in the transfer function, also allows the temporal progression of the perfusion to be simulated continuously. A true, memory-intensive and costly 4D visualization is not required for this, since only one or two volume data records with the maximal and time values in conjunction with the transfer function have to be accessed.

FIG. 4 shows the use of different windowing or a different timing of the step in the transfer function in the four and costly illustrations elements a, b, c and d. In FIG. 4a, the step in the transfer function has already been set at an early time, so that the values for all later times are masked out. Thus, FIG. 4a shows an image in which only vessels highlighted with a contrast agent at an early time can be recognized. By shifting the step in the transfer function to later times, the further highlighting can be observed (FIG. 4b/c).

Figure 4A:
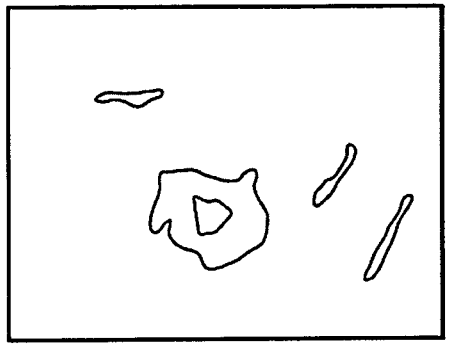
FIG. 4 shows an example of a simulation of the temporal progression, which can be generated with the method according to an embodiment of the present invention.
Figure 4B:
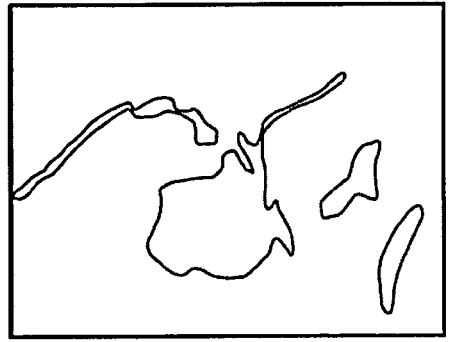
Figure 4C:
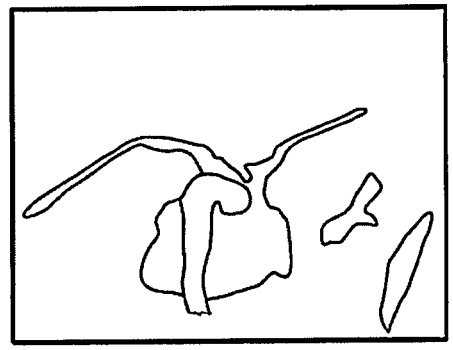
Figure 4D:
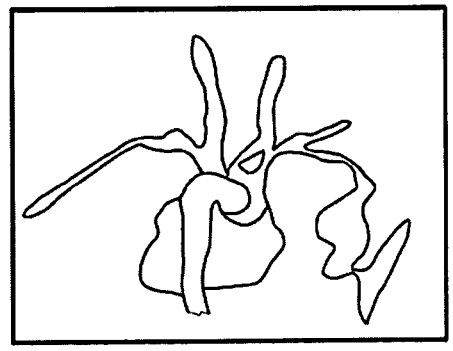

FIG. 4d finally shows an illustration obtained with a step shifted very far back temporally or without a step in the transfer function. In reality, this illustration in FIG. 4 is of course much finer since substantially more intermediate steps can be illustrated on the basis of the different color coding. In this case, the user can interactively shift the step in the transfer function. Furthermore, an automatic shift can also be provided for the transfer function, so that a temporally smooth shift of the transfer function is carried out in the illustration following the appropriate input command from the user.

Figure 6A:
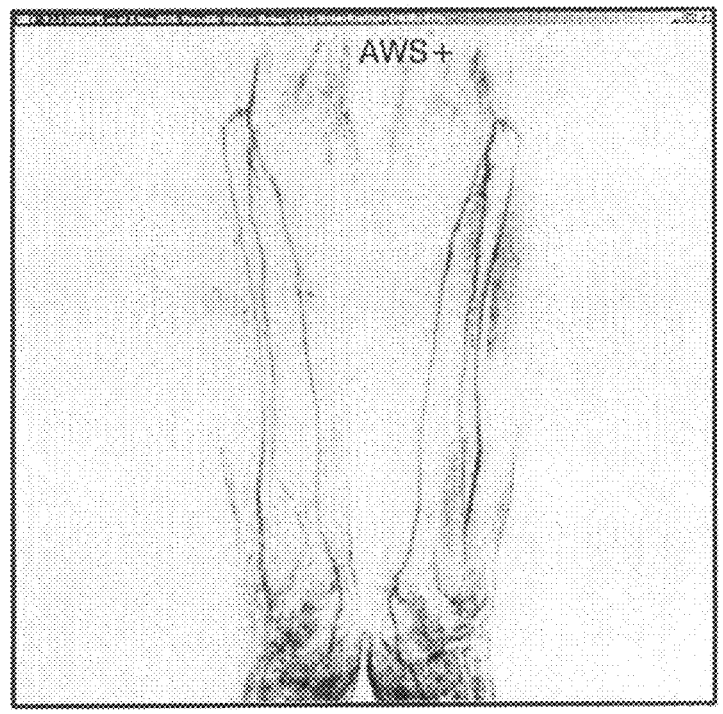
FIG. 6 shows an example of masking out the venous part of the vascular system.
Figure 6B:
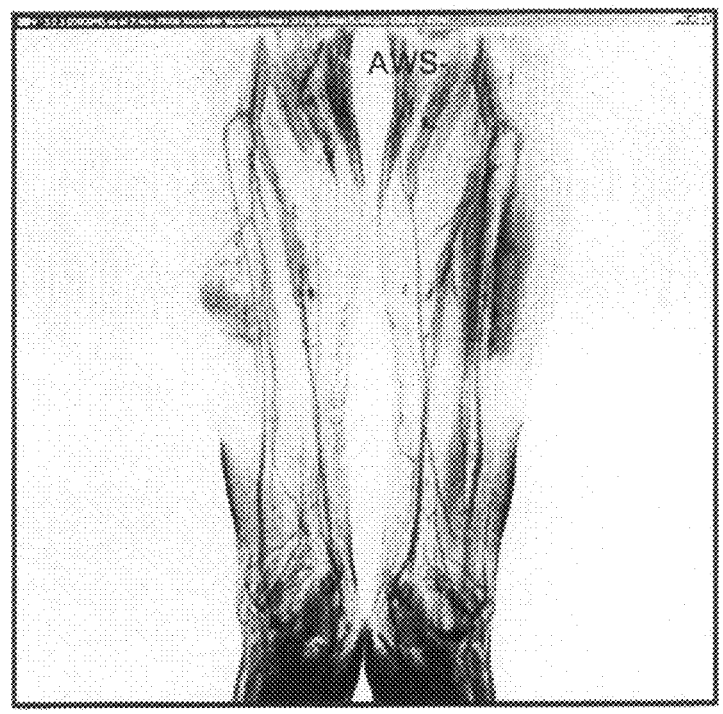

FIG. 5 shows a further example of a two-dimensional transfer function, which can be used in the embodiments of the present invention. In this example, all time values below a given step are coded in red, while all later values are masked out. By a suitable choice of the time of the step, that is to say by interactive windowing of the TTP values, the venous part of the vessel can be masked out, as illustrated in FIG. 6a. By comparison, the overall blood stream is visualized in FIG. 4b without such masking-out. Optionally, early TTP times can be mapped onto red hues (arterial) and later TTP times can be mapped onto blue hues (venous) in this case, so that the type of blood vessel is apparent from the color. This technique allows interactive 3D artery-vein separation.

Embodiments of the present invention have been explained and discussed, in particular, with respect to the use of a two dimensional transfer function based on scalar and time values. Of course, this procedure can be extended to multidimensional transfer functions, which comprise more than two dimensions. An example of this is the use of a further value, in particular when the sequence of tomographic volume data records comprises a plurality of volume data records from different tomographic imaging devices for each time. In this manner, additional characteristics can be determined as parameter for each voxel and imaged with aid of the transfer function.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

I claim:

1. A method for visualizing a sequence of tomographic volume data records for medical imaging, the tomographic volume data records being recorded in temporal sequence with administration of contrast agents in vessels in an object volume such that at least one temporal sequence of measured signal values is present for each voxel of the object volume, the method comprising:
   determining, for each voxel, at least one extremal value and at least one time value from the temporal sequence of the measured signal values, the time value indicating a time lag of the extremal value or of a value derived therefrom compared to a fixed time during the recording of the volume data records;
   assigning, via a multi-dimensional transfer function, each combination of time value and extremal value or value derived therefrom a color value and an opacity value, the color value being a measure of the magnitude of the time value, and the opacity value being a measure of the magnitude of the extremal value or the value derived therefrom;
   assigning each voxel of the object volume a color value and opacity value by applying the transfer function to the determined time and extremal values or values derived therefrom; and
   displaying the voxels with the respective color and opacity values using volume rendering.

2. The method as claimed in claim 1, wherein the transfer function is a linear association of extremal values and opacity values.

3. The method as claimed in claim 1, wherein opacity values assigned to small extremal values are smaller than opacity values assigned to large extremal values.

4. The method as claimed in claim 2, wherein opacity values assigned to small extremal values are smaller than opacity values assigned to large extremal values.

5. The method as claimed in claim 1, wherein the transfer function assigns different color values to different time values.

6. The method as claimed in claim 2, wherein the transfer function assigns different color values to different time values.

7. The method as claimed in claim 3, wherein the transfer function assigns different color values to different time values.

8. The method as claimed in claim 1, wherein the multi-dimensional transfer function is an at least two-dimensional transfer function.

9. The method as claimed in claim 1, further comprising:
fixing a time value; and
masking out voxels having time values either above or below the fixed time value in the image by the transfer function.

10. The method as claimed in claim 2, further comprising:
fixing a time value; and
masking out voxels having time values either above or below the fixed time value in the image by the transfer function.

11. The method as claimed in claim 3, further comprising:
fixing a time value; and
masking out voxels having time values either above or below the fixed time value in the image by the transfer function.

12. The method as claimed in claim 4, further comprising:
fixing a time value; and
masking out voxels having time values either above or below the fixed time value in the image by the transfer function.

13. The method as claimed in claim 5, further comprising:
fixing a time value; and
masking out voxels having time values either above or below the fixed time value in the image by the transfer function.

14. The method as claimed in claim 1, further comprising:
fixing a time value; and
assigning voxels having time values above the fixed time value a different constant color value than voxels having time values below the fixed time value.

15. The method as claimed in claim 2, further comprising:
fixing a time value; and
assigning voxels having time values above the fixed time value a different constant color value than voxels having time values below the fixed time value.

16. The method as claimed in claim 5, further comprising:
fixing a time value; and
assigning voxels having time values above the fixed time value a different constant color value than voxels having time values below the fixed time value.

17. The method as claimed in claim 14, wherein voxels having time values above the fixed time value assigned a blue color value, and voxels having time values below the fixed time value are assigned a red color value.

18. The method as claimed in claim 9, further comprising:
interactively or automatically increasing or decreasing, by a user, the fixed time value.

19. The method as claimed in claim 14, further comprising:
interactively or automatically increasing or decreasing, by a user, the fixed time value.

20. The method as claimed in claim 17, further comprising:
interactively or automatically increasing or decreasing, by a user, the fixed time value.

21. A tangible computer readable medium including program segments for, when executed on a computer device, causing the computer device to implement the method of claim 1.

22. A method for visualizing a sequence of tomographic volume data records for medical imaging, the method comprising:
determining, for each voxel of an object volume, at least one extremal value and one time value based on measured signal values, the time value being indicative of a time lag of the extremal value or a value derived therefrom relative to a fixed time value;
assigning, via a multi-dimensional transfer function, a color value and an opacity value to each combination of time value and extremal value or value derived therefrom, the color value being indicative of a magnitude of the time value, and the opacity value being indicative of a magnitude of the extremal value or the value derived therefrom;
assigning a color value and opacity value to each voxel of the object volume by applying the transfer function to the determined time and extremal values or values derived therefrom; and
displaying the voxels using the respective color and opacity values.

23. The method as claimed in claim 22, further comprising:
fixing the time value; and
masking out voxels having time values either above or below the fixed time value in the image by the transfer function.

24. The method as claimed in claim 22, further comprising:
fixing a time value; and
assigning voxels having time values above the fixed time value a different constant color value than voxels having time values below the fixed time value.

25. The method as claimed in claim 22, further comprising:
interactively or automatically increasing or decreasing, by a user, the fixed time value.

26. A tangible computer readable medium including program segments for, when executed on a computer device, causing the computer device to implement the method of claim 22.

* * * * *